United States Patent [19]

Baehr

[11] 4,033,349
[45] July 5, 1977

[54] CORNEAL SEAL DEVICE

[75] Inventor: Edward F. Baehr, Berea, Ohio

[73] Assignee: The United States of America as represented by the Administrator of the National Aeronautics and Space Administration, Washington, D.C.

[22] Filed: Apr. 13, 1976

[21] Appl. No.: 676,433

[52] U.S. Cl. .......................... 128/303 R; 128/1 R
[51] Int. Cl.² .................. A61F 9/00; A61B 17/00
[58] Field of Search ............... 128/1 R, 276, 303 R, 128/305, 347

[56] References Cited

UNITED STATES PATENTS

| 3,074,407 | 1/1963 | Moon et al. | 128/303 R |
| 3,263,683 | 8/1966 | Uddenberg | 128/303 R |
| 3,323,846 | 6/1967 | Boddy | 128/1 R X |
| 3,589,363 | 6/1971 | Banko et al. | 128/303 R X |
| 3,618,594 | 11/1971 | Banko | 128/303 R X |
| 3,732,858 | 5/1973 | Banko | 128/305 X |
| 3,812,855 | 5/1974 | Banko | 128/276 |
| 3,902,495 | 9/1975 | Weiss et al. | 128/276 |
| 3,930,505 | 1/1976 | Wallach | 128/276 X |

Primary Examiner—Channing L. Pace
Attorney, Agent, or Firm—N. T. Musial; J. A. Mackin; John R. Manning

[57] ABSTRACT

A corneal seal device is provided which, when placed in an incision in the eye, permits the insertion of a surgical tool or instrument through the device into the eye.

The device includes a seal chamber which opens into a tube which is adapted to be sutured to the eye and serves as an entry passage for a tool. A sealable aperture in the chamber permits passage of the tool through the chamber into the tube and hence into the eye. The chamber includes inlet ports adapted to be connected to a regulated source of irrigation fluid which provides a safe intraocular pressure.

9 Claims, 7 Drawing Figures

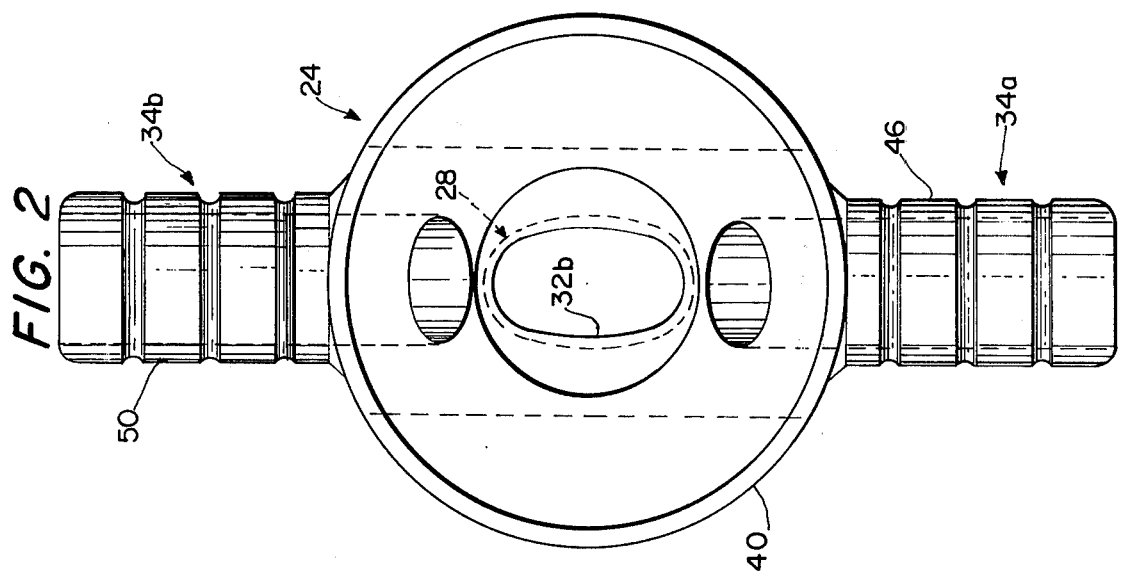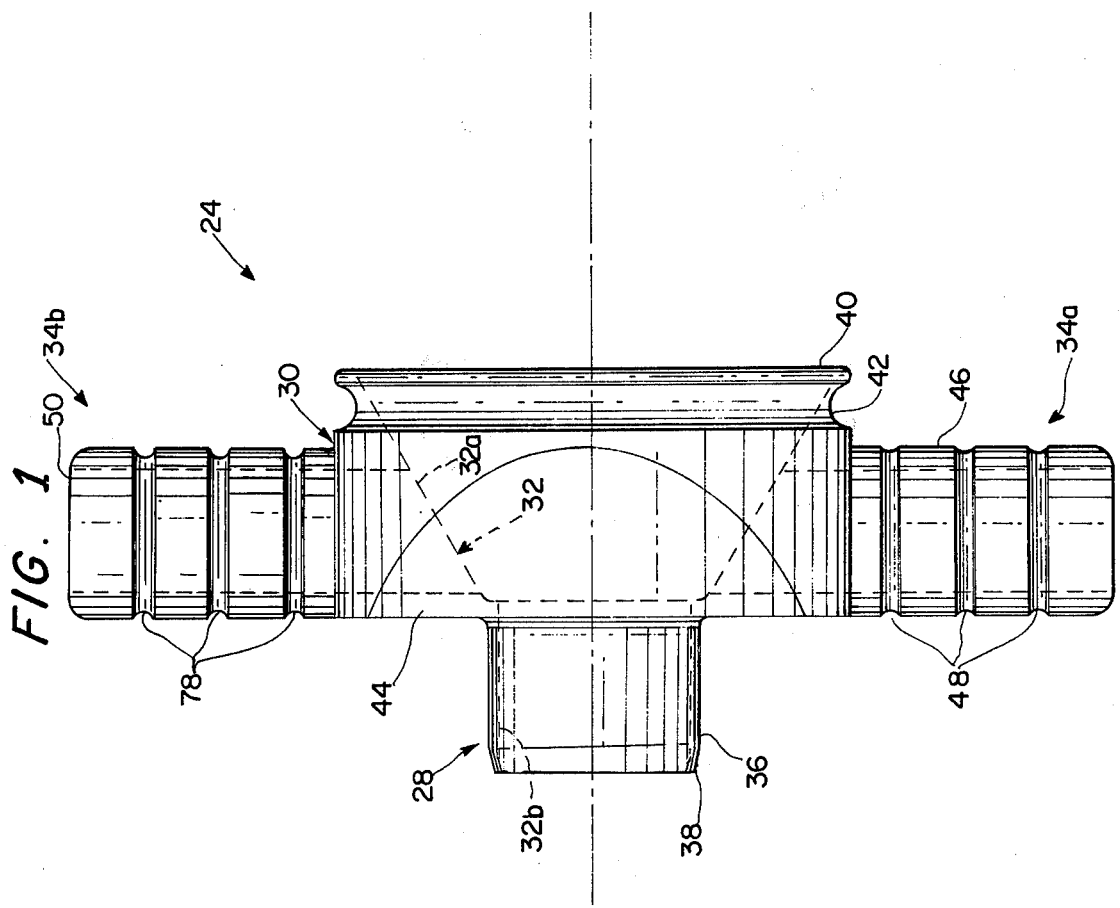

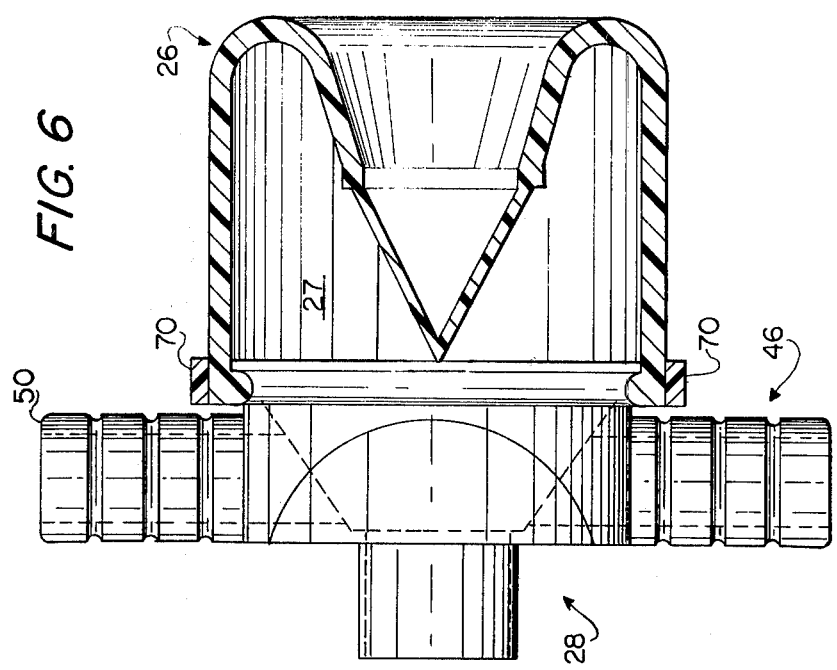
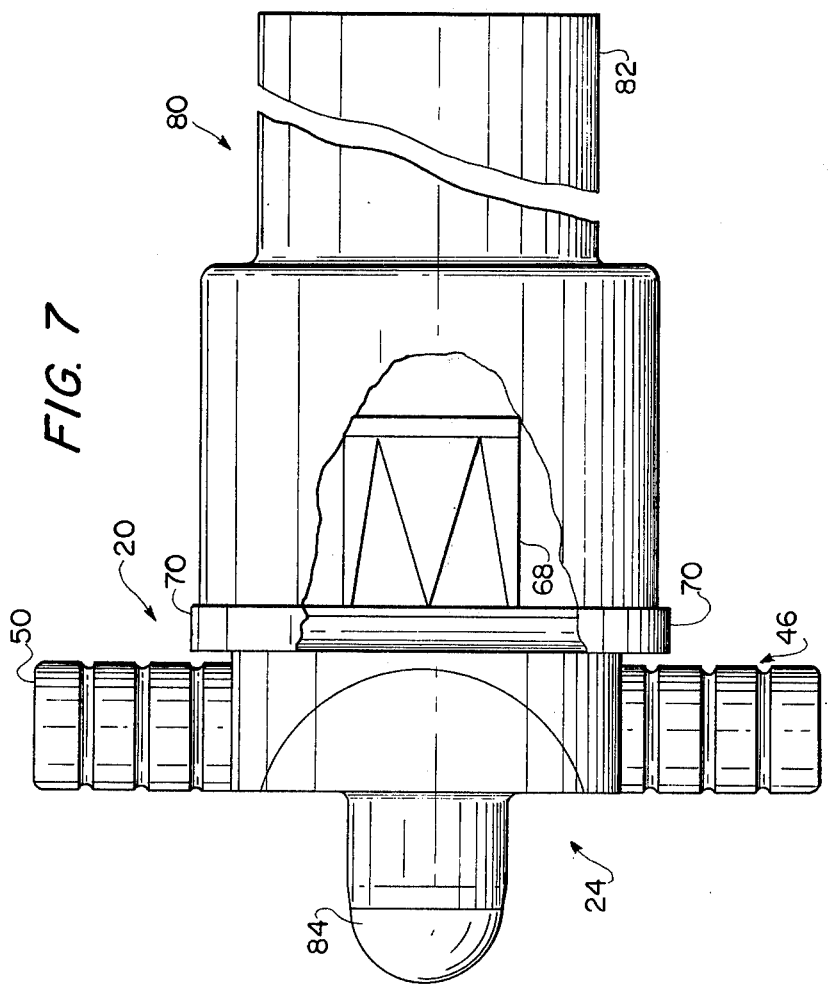

CORNEAL SEAL DEVICE

ORIGIN OF THE INVENTION

This invention was made by an employee of the United States Government and may be manufactured or used by or for the Government without the payment of any royalties thereon or therefor.

BACKGROUND OF THE INVENTION

1. Field of the Invention

This invention relates to devices used for eye surgery and, more particularly, to a device for assisting in the insertion of a tool or like instrument into the eye while maintaining the pressure of the eye at a safe level.

2. Description of the Prior Art

The eye is a relatively delicate and easily damaged part of the body. Therefore, eye surgery must be undertaken with great care and the instruments used during eye surgery to repair the eye must not themselves cause further eye damage.

In general, prior art surgical procedures provide for introducing the surgical tool itself directly into an incision in the eye. Sometimes a silicon sheath surrounds the tool but this sheath moves with the tool and does not insulate the eye wall from the tool. Since the instrument is introduced directly into the eye, the instrument is prone to rub against immediately adjacent eye tissue. Such rubbing against a localized area of the eye can cause eye trauma.

Further, such devices suffer from several other disadvantages. The incision, once made, is sometimes very difficult to locate. Thus, much probing is required before the tool can be introduced into the eye. Such probing can also cause eye trauma. Also, with such a technique it is difficult to assure an adequate supply of irrigation fluid to the eye to maintain safe interocular pressure. While there have been attempts to incorporate eye irrigation systems into the surgical instrument itself, this approach suffers several important disadvantages. For example, this approach does not provide adequate interocular pressure level control. Additionally, such an approach adds to the overall dimensions of the instrument and this increase in bulk is clearly not desirable when working with the eye. Also, with this approach, nothing prevents the leakage of interocular fluid from between the incision and the instrument. Such leakage can become more pronounced as the tool is manipulated, since tool manipulation can spread apart the tissue surrounding the incision.

An example of a prior art eye surgical instrument which provides irrigation can be found in U.S. Pat. No. 2,480,737. Other prior art surgical devices provide for a sleeve that can be inserted into an incision in the eye and sutured in place. Such devices are found, for example, in U.S. Pat. Nos. 3,528,425; 3,659,607; 3,732,858. However, among other disadvantages, such devices do not provide fluid irrigation for maintaining safe interocular pressure.

SUMMARY OF THE INVENTION

The present invention provides for a corneal sealing device for use in eye surgery that overcomes the disadvantages associatd with the prior art devices noted hereinabove. The device provides easy entry of a tool therethrough into the eye, without causing trauma to the eye. Further, the device permits the required quantity of irrigation fluid flow into the eye in order to maintain safe interocular pressure. Moreover, the corneal seal device prevents undue leakage of fluid while allowing surgical tools to freely enter the eye and to move through a wide range of angular positions.

In accordance with a preferred embodiment of the invention, a corneal seal device is presented for assisting in eye surgery. The device comprises a tube member adapted to be introduced into the eye and defining an entry passageway for a surgical tool. The device also includes a seal chamber in fluid communication with one end of the tube member. A too entry is provided in the seal chamber for sealably engaging a surgical tool introduced into the chamber for passage therethrough into the tube member. Also, connections are provided between the seal chamber and a source of irrigation fluid for maintaining the interocular pressure at a desired level.

Additional features and advantages of the invention will be set forth in, or apparent from, the detailed description of the preferred embodiments of the invention found hereinbelow.

BRIEF DESCRIPTION OF THE DRAWINGS

FIG. 1 is an enlarged side view of the support member of the invention;

FIG. 2 is an enlarged bottom plan view of the support member as depicted in FIG. 1;

FIG. 6 is an enlarged cross-sectional view of the seal member mounted to a partially cut-away, enlarged side view of the support member;

FIG. 7 is an enlarged side elevational view of a trocar partially cut away inserted into the apparatus of the invention used to permit easy insertion into the incision.

DETAILED DESCRIPTION OF THE PREFERRED EMBODIMENTS

Figure 3:
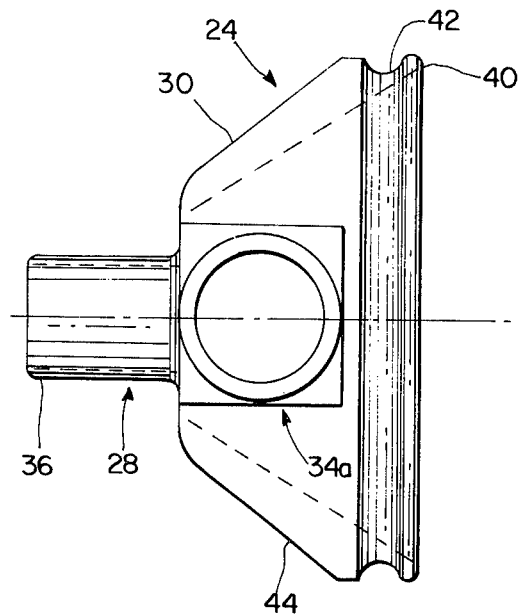
FIG. 3 is an enlarged end view of the support member as depicted in FIG. 1.

As described above, the corneal seal device of the invention includes a tube which is adapted to be sutured to the eye and which serves as an entry passageway for a tool and a seal chamber in fluid communication with the tube and adapted to be connected to a source of irrigation fluid for the eye. The seal device is preferably constructed of two basic components, which, for convenience, are referred to as a support member and a seal member. The support member which is denoted 24 and is illustrated in FIGS. 1 to 3, includes a tube member 28 formed integrally therewith. The seal member, which is denoted 26, and is illustrated in FIGS. 4 to 9, is mountable to support element 24 to form seal chamber 27, as shown in FIG. 6. The two basic components will be described individually before considering the device as a whole.

Referring particularly to FIGS. 1 to 3, member 24 comprises a cylindrical eye contacting tube member 28, a body portion 30 formed integrally with cylindrical portion 28, a passageway 32 extending through portions 28 and 30, and comprising a conical pat 32a and a cylindrical part 32b, and irrigation members 34a and 34b in fluid communication with the conical part 32a of passageway 32. As can best be seen in FIGS. 1 and 2 taken together, the shape of cylindrical portion 28 is generally a right elliptical cylinder which, in an exemplary embodiment, is about 0.1 inches high and has a major diameter of about 0.14 inches and a minor diameter of about 0.082 inches. Cylindrical passageway 32b extends coaxially through cylindrical portion 28 and the wall 36 formed between the inner surface of passageway 32 and the outer surface of cylindrical portion 28 is quite thin, e.g., about 0.01 inches thick in an exemplary embodiment. The edge 38 of wall 36 is generally beveled. It should be understood that the cross-sectional shape of cylindrical portion 28 of support element 24 can be varied to accommodate a variety of surgical instruments as well as the particular angular movement requirements of these instruments. Further, the size of passageway 32 must be such as to accommodate the instrument while providing clearance between the instrument and the sides of wall 36 such as to permit irrigation fluid to pass therebetween.

A circumferential recess 42 is formed in the base of body portion 30 between the related side walls 44 and an outer lip or rim 40. Recess 42 has generally a semicircular cross section (FIG. 1).

Formed integrally with body portion 30 of support element 24 are the irrigation members 34a and 34b referred to above. Members 34a and 34b comprise rigid elongate tubes 50 and 46 respectively, which, as noted, have respective passageways therethrough in fluid communication with passageway 32 of supporting member 24. Tubes 46 and 50 extend outwardly from body portion 30 perpendicular to the axis of passageway 32. Elongate tubes 46 and 50 have a plurality of spaced, circumferential recesses 48 and 78, respectively, located along their lengths. Respective flexible tubes (not shown) leading to a source of irrigation fluid (not shown) are forced over tubes 46 and 50 and retained by recesses 48 and 78. In the exemplary embodiment referred to, tubes 46 and 50 have outside diameters of about 0.11 inches and are approximately 0.25 inches in length.

It is noted that support member 24 can be composed of a clear material such as, for example, a polycarbonate, so that the eye can be viewed therethrough.

Figure 4:
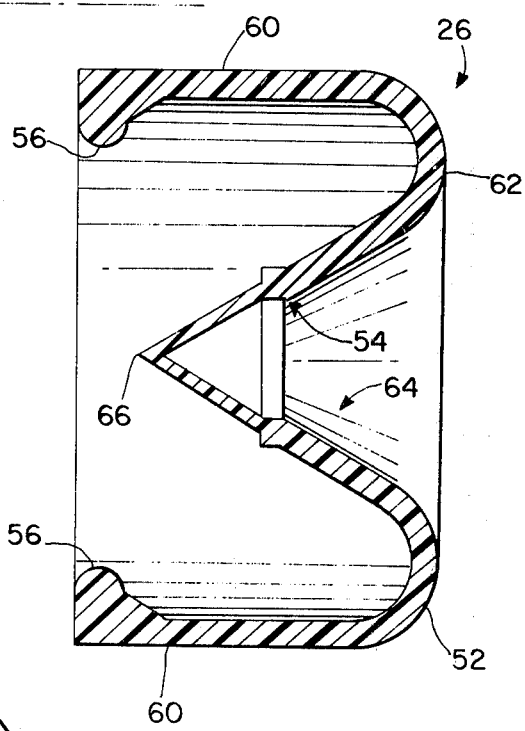
FIG. 4 is an enlarged cross-sectional view of the sealing member of the invention.
Figure 5:
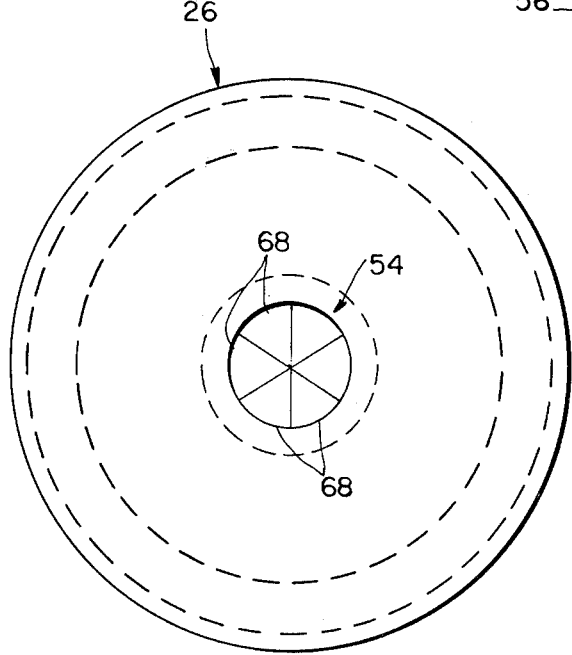
FIG. 5 is an enlarged plan view of the sealing member as depicted in FIG. 4.

Seal member 26, which is best seen in FIGS. 4 and 5, comprises a generally symmetrical cup-shaped member 52 with an access aperture 54 located on the axis of symmetry of member 52. Cup-shaped member 52 is, as shown in FIG. 4, generally M-shaped in cross-section and includes a cylindrical side wall 60 having an inwardly extending annular lip 56 formed at the edge of the inner surface thereof. The shape of lip 56 is the reciprocal of that of recess 42 of support member 24 and is received by the recess 42 when seal member 26 is in its operating position.

Cup-shaped member 52 further includes an annular rear wall 62 and inwardly extending conical portion 64 in which access aperture 54 is centrally located. Aperture 54 is normally closed by a plurality of inwardly extending flexible closure members 68 which are of triangular shape and converge to an apex 66. The resilient or flexible nature of closure member 68 permits them to be pushed aside when a trocar or tool is inserted into aperture 54. When the instrument is in position, closure elements 68 engage the shaft thereof providing a sealing effect.

Seal member 26 is generally comprised of a clear material such as, for example, silicone, that is also flexible. Thus, the eye can be viewed through seal 26 and the movement of the surgical instrument while in seal 26 is not inhibited.

A band 70 (shown sectioned in FIG. 6), which can be comprised of, for example, plastic, metal or rubber is provided for securing seal member 26 to support member 24. Once the lip 56 of seal 26 is snapped over end 40 of support member 26 (FIG. 6) so that lip 56 is received in recess 42, band 70 is placed around side wall 60 of seal 26 adjacent support member 24. Thus, band 70 holds lip 56 in recess 42.

Finally, an exemplary embodiment of a trocar 80 (FIG. 7) to be used with the corneal seal is provided. It is generally contemplated that trocar 80 can include a handle 82 for ease of insertion & removal. Generally, handle 82 is also comprised of a clear material, such as a clear polycarbonate, so as not to obstruct a view of the eye.

Probe 84 is generally comprised of a non-clear material, such as white teflon. Other colors can be selected so as to contrast with that portion of the eye into which probe 84 is inserted.

The operation of the corneal seal is as follows. Seal member 26 is snapped over support member 24 so that lip 56 rests in recess 42. Band 70 is placed over seal member 26 so that seal 26 is secured to support 24. Flexible tubes (not shown) leading to a source of irrigation fluid are connected to irrigation elements 34a and 34b. The use of two flexible tubes eliminate undesirable torque that is placed on the corneal seal device when only one flexible tube is connected thereto. Next an incision is made in the eye. A trocar with a tapered probe is inserted through access aperture 54 and forces apart closure members 68. The probe is pushed completely through passageway 32 until it extends out of cylindrical portion 28 of support member 24. The probe is used to locate the incision and to guide the cylindrical portion 28 of support 24 into the incision. The corneal seal is sutured to the eye. Sutures can be looped about irrigation members 34a and 34b. Then a small pressure regulator is activated to provide irrigation fluid to irrigation members 34a and 34b. Thus, the desired interocular pressure can be maintained. As the insertion probe is removed from the eye and from access aperture 54, closure members 68 converge into apex 66. Thus, the corneal seal is sealed, preventing the loss of irrigation fluid. Other tools can now be introduced through access aperture 54 into the eye to perform the desired eye surgery.

At the completion of surgery, the corneal seal is removed and the incision in the eye is sutured for proper healing.

Although the present invention has been described relative to an exemplary embodiment thereof, it will be understood by those skilled in the art that variations and modifications can be effected in these embodiments without departing from the scope and spirit of the invention.

I claim:
1. A corneal seal device for assisting in eye surgery, said device comprising:
   a tube member adapted to be introduced into the eye and defining an entry passageway for a surgical tool; and
   means defining a seal chamber in fluid communication with the one end of said tube member and including sealable tool entry means therein for sealably engaging a surgical tool introduced into said chamber for passage therethrough into said tube member, and means for connecting said tube member to a source of irrigation fluid for maintaining the intraocular pressure at a desired level.

2. A corneal seal device in accordance with claim 1 wherein said seal chamber defining means comprises first and second detachable portions, said first portion comprising a support member integral with said tube member and said second portion comprises a seal member detachable connected to said support member.

3. A corneal seal device in accordance with claim 2 wherein said seal member includes a central recessed conical wall therein, said sealable tool entry means forming the innermost end of said wall and including a plurality of flexible closure members.

4. A corneal seal device in accordance with claim 2 wherein the portion of said seal chamber defined by said support member includes side walls which slope inwardly between the seal chamber and the passageway defined by said tube member.

5. Corneal seal device in accordance with claim 2 wherein said support member is comprised of a clear polycarbonate material.

6. Corneal seal device in accordance with claim 2 wherein said seal member has generally a cup shape with a radially inwardly extending annular lip.

7. Corneal seal device in accordance with claim 6 wherein said support member has a recessed portion for receiving said lip of said seal member and further including a band for securing said seal member onto said support member once said lip is received by said recess.

8. Corneal seal device in accordance with claim 2 wherein said seal member is comprised of a clear silicone material.

9. Corneal seal device in accordance with claim 1 wherein said means for connecting said tube member to a source of irrigation fluid includes at least two irrigation tubes integrally molded with and extending outwardly from said tube member for counterbalancing the torque placed on said tube member by said irrigation tubes individually.

* * * * *